United States Patent [19]

Deguchi et al.

[11] Patent Number: 5,025,069
[45] Date of Patent: Jun. 18, 1991

[54] MILD ALKYL GLYCOSIDE-BASED DETERGENT COMPOSITIONS, FURTHER COMPRISING TERPENE AND ISOTHIAZOLONE DERIVATIVES

[75] Inventors: Katsuhiko Deguchi; Kozo Saito; Hiroyuki Saijo; Masaki Tosaka, all of Utsunomiya, Japan

[73] Assignee: Kao Corporation, Tokyo, Japan

[21] Appl. No.: 446,815

[22] Filed: Dec. 6, 1989

[30] Foreign Application Priority Data

Dec. 19, 1988 [JP] Japan ............................. 63-319906
Jan. 9, 1989 [JP] Japan ................................. 1-2570

[51] Int. Cl.$^5$ ..................... C11D 1/83; C11D 1/66; C11D 3/18; C11D 3/28
[52] U.S. Cl. ............................. 252/174.17; 252/171; 252/174.11; 252/174.21; 252/547; 252/550; 252/551; 252/552; 252/553; 252/555; 252/556; 252/558; 252/559; 252/DIG. 1; 252/DIG. 5; 252/DIG. 13
[58] Field of Search ................. 252/174.17, 162, 171, 252/174.11, 174.21, 547, 550–556, 558, 559, DIG. 1, DIG. 5, DIG. 13

[56] References Cited

U.S. PATENT DOCUMENTS

| 4,243,403 | 1/1981 | Lewis et al. | 71/67 |
| 4,414,128 | 11/1983 | Goffinet | 252/111 |
| 4,483,779 | 11/1984 | Llenado et al. | 252/135 |
| 4,483,780 | 11/1984 | Llenado | 252/135 |
| 4,663,069 | 5/1987 | Llenado | 252/117 |

FOREIGN PATENT DOCUMENTS 64-69699 3/1989 Japan .
8702698 5/1987 World Int. Prop. O. .

Primary Examiner—A. Lionel Clingman
Assistant Examiner—A. Beadles-Hay
Attorney, Agent, or Firm—Oblon, Spivak, McClelland, Maier & Neustadt

[57] ABSTRACT

A low irritant, mild detergent composition is disclosed. The detergent composition comprises, as essential components, (a) alkyl glycoside, (b) a surface active agent containing sulfate and/or sulfonate group, (c) an amine oxide, and (d) an ethoxylated surface active agent at a specific ratio. The detergent composition is low irritant, has excellent foaming ability and detergency, and yet is easily rinsed out and at the same time provides a pleasant feeling to the hands during use. It can be used as laundry detergents, dishwashing detergents, as well as detergents for use with household products, and hair and body. Further, a detergent composition comprising (e) a terpene type hydrocarbon and (f) 3-isothiazolone or its derivative in addition to the above components (a)-(d) is more valuable in practical use owing to preventing solution color and odor from being deteriorated during storage for a prolonged period of time.

4 Claims, No Drawings

MILD ALKYL GLYCOSIDE-BASED DETERGENT COMPOSITIONS, FURTHER COMPRISING TERPENE AND ISOTHIAZOLONE DERIVATIVES

BACKGROUND OF THE INVENTION

1. Field of the Invention

This invention relates to a detergent composition, and, more particularly, to a detergent composition which remarkably alleviates irritation and damage to the hair and the skin. The composition has excellent foaming ability and detergency, and is easily rinsed out and at the same time provides an agreeable feel to the hands during use.

2. Description of the Background Art

Because of the increased awareness concerning safety of the human body in recent years, a number of attempts have been undertaken to achieve mildness to the skin in the manufacture of laundry detergents, dishwashing detergents, detergents for use with household products, as well as those for the hair and the body. An example of such attempts is to adjust the pH of detergent compositions to a weakly acidic range, i.e., pH 5-6, which is near the pH of the human skin, thereby obtaining mildness to the skin. Another example is the use of a low irritant detergent base as a major detergent component. Amino acid type or alkylphosphate type surface active agents are used as low irritant detergent bases for this purpose (Japanese Patent Publication Nos. 40125/1975, 426023/1976, 9033/1980, and 27319/1983).

Although these surface active agents are low irritant, they have drawbacks such as insufficient foaming ability and detergency, poor solubility, and the like when used alone. Sodium alkylbenzene sulfonates have conventionally been used as a detergent base for detergent compositions. Although they have excellent detergency, their strong defatting action is liable to cause skin roughening.

For these reasons, sodium alkylethoxy sulfates which are less irritant have currently been used as a detergent base for dishwashing detergent compositions. Their use in combination with tertiary amine oxides, higher fatty acid diethanolamides, etc., as auxiliary surface active agents, has promoted various performances, providing dishwashing detergent compositions with reduced irritation to the skin.

In spite of these efforts for producing detergent compositions which are less irritant and mild to the skin, the level of improvement hitherto achieved is not yet satisfactory.

Alkyl glycosides, which are saccharide-derived surface active agents, are low irritant, nonionic surface active agents. Even though nonionic in nature, alkyl glycosides not only produce stable foams by themselves but also are known to act as foam stabilizers for anionic surface active agents. Because of this, a great deal of attention has been given to alkyl glycosides in recent years. Japanese Patent Laid-open No. 104625/1983, for example, discloses a foaming surfactant composition comprising an anionic surface active agent and an alkyl glycoside. Japanese Patent Laid-open No. 74999/1987 describes a low irritant liquid detergent composition for dishwashing use having superior foaming capability and detergency which comprises an alkyl glycoside, an anionic surface active agent, and a fatty acid alkanolamide. Japanese Patent Laid-open No. 186429/1983 reports a foaming surfactant composition comprising an alkyl glycoside, an anionic surfactant, and a fatty acid alkanolamide or an amine oxide. Japanese Patent Laid-open No. 500725/1987 discloses a viscosity-increased liquid detergent composition comprising an alkyl monoglycoside and an anionic surfactant. Also, Japanese Patent Laid-open No. 197495/1987 describes a liquid detergent composition for clothing comprising a nonionic surfactant, an anionic surfactant, and an alkyl glycoside. These detergent compositions, although exhibiting performances better than conventional detergent compositions using polyoxyethylenealkyl ethers as a major component, are not yet satisfactory, especially in their rinse-out performance and in the feel which they impart to the hands during washing. These detergent compositions also have problems of deterioration in their colors and odors when they are stored for a prolonged period of time, resulting in damages to their qualities.

In view of this situation, the present inventors have conducted extensive studies to make the best use of the superior characteristics of alkyl glycosides. As a result, the present inventors found that a combined use of a surface active agent having a sulfate and/or sulfonate group and an amine oxide and ethoxylated nonionic surface active agent together with an alkyl glycoside compound lessened the irritation to the skin, promoted detergency and foaming ability, and, at the same time, brought about improved rinse-out performance and better feeling to the hands during washing. The inventors also found that the detergent compositions to which a terpene type hydrocarbon selected from mono-terpene and sesqui-terpene, and 3-isothiazolone and/or its derivative are incorporated in addition to the above components, exhibited remarkably reduced deterioration in their solution colors and odors during storage over a prolonged period of time. Such findings have led to the completion of the present invention.

SUMMARY OF THE INVENTION

Accordingly, an object of this invention is to provide a detergent composition comprising:

(a) 1–60% by weight of an alkyl glycoside represented by formula (I):

$$R_1(OR_2)_xG_y \qquad (I)$$

wherein $R_1$ represents a linear or branched alkyl, alkenyl, or alkylphenyl group having 8 to 18 carbon atoms, $R_2$ represents an alkylene group having 2 to 4 carbon atoms, G is a moiety derived from a reducing saccharide having 5 to 6 carbon atoms, x is an average value of 0–5, and y is an average value of 1.0–1.42;

(b) 0.1–40% by weight of a surface active agent comprising a sulfate group, a sulfonate group, or the both;

(c) 0.1–10% by weight of an amine oxide represented by formula (II):

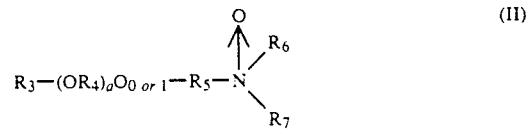

wherein $R_3$ represents a linear or branched alkyl or alkylamide group having 8 to 18 carbon atoms, $R_4$ represents an alkylene group having 2 to 3 carbon atoms, a denotes a number of 0–30, $R_5$ represents an alkylene group having 0 to 5 carbon atoms, and $R_6$ and $R_7$, which may be the same or different, represent a member selected from the group consisting of an alkyl group having 1 to 12 carbon atoms, an alkanol group having 1 to 3 carbon atoms, a group $—(C_2H_4O)_{1-6}H$, and a mixture thereof, and (d) 0.1–10% by weight of an ethoxylated nonionic surface active agent; and wherein the ratio by weight of $[(b)+(c)]/(a)$ is in the range of 1/25–10/1 and the ratio by weight of $(c)/(b)$ is 1/10–3/1.

In a preferred embodiment of the present invention, the detergent composition further comprises, in addition to the above essential components;

(e) 0.01–3% by weight of a terpene type hydrocarbon selected from the group consisting of mono-terpene and sesqui-terpene, and (f) 0.0001–0.1% by weight of one or more of 3-isothiazolones represented by formulae (VI) and (VII), or their derivatives,

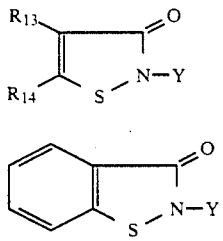

wherein $R_{13}$ and $R_{14}$ individually represent a hydrogen atom, a halogen atom, or a $C_{1-5}$ alkyl group, and Y represents a hydrogen atom or $C_{1-18}$ alkyl group.

Other objects, features and advantages of the invention will hereinafter become more readily apparent from the following description.

DETAILED DESCRIPTION OF THE INVENTION AND PREFERRED EMBODIMENTS

Alkyl glycoside, component (a), is used as a major detergent component in the composition of the present invention. The value of x in formula (I) defined as an average value of 0 to 5 is a factor controlling the solubility and the crystallization of component (a). There is a tendency that the higher the value of x, the higher is the water-solubility and the lower the crystallization. A preferable value of x is 0 to 2. In case the mean value of y in formula (I) is larger than 1, i.e., when the alkyl glycosides comprise compounds of formula (I) having di- or polysaccharide chains as hydrophilic groups, the component (a) can be a mixture of compounds having various types of saccharide bond, including 1-2, 1-3, 1-4, 1-6, α-pyranoside, β-pyranoside bonds, and furanoside bond. A preferable value of y is a mean value of 1.0–1.42, with an especially preferable range being 1.10–1.40. The value of y is determined by the proton-NMR method. For $R_1$ defined as a linear or branched alkyl, alkenyl, or alkylphenyl group having 8 to 18 carbon atoms in formula (I), those having 10–14 carbon atoms are preferable from the aspect of good solubility foaming capability, and detergency. For $R_2$ of formula (I), an alkylene group of a 2–4 carbon atom content, especially of a 2–3 carbon atom content, are preferable in view of their good water solubility. G in formula (I) depends for its structure on the saccharide from which it is derived, i.e., on whether the saccharide is mono- or polysaccharide. Given as examples of monosaccharides are glucose, fructose, galactose, xylose, mannose, lixysose, arabinose, and their mixtures. Polysaccharides may be maltose, xylobiose, iso-maltose, cerobiose, gentibiose, lactose, sucrose, nigerose. turanose, raffinose, gentianose, merezitose, and their mixtures. Among monosaccharides, glucose and fructose are desirable in view of their ready availability and low cost. Maltose and sucrose are preferable among the polysaccharides.

Component (a) is contained in the detergent composition in an amount of 1–60% by weight, and more preferably 10–40% by weight.

Enumerated as preferably examples of component (b), a surface active agent having a sulfate and/or a sulfonate group, are polyoxyethylene alkyether sulfate, alkylbenzene sulfonate, α-olefin sulfonate, alkane sulfonate, α-sulfonated fatty acid derivatives, sulfobetaine, acylmethyltaurin, and the like. They can be used alone or in combination of two or more of them.

Among these, polyoxyethylene alkylether sulfates, especially those represented by the following formula (III), are preferable from the aspect of mildness to the skin, $$R_8O(CH_2CH_2O)_nSO_3M \qquad (III)$$

wherein $R_8$ represents an alkyl or alkenyl group having 10 to 18 carbon atoms, M represents an alkali metal, ammonium, or alkanol amine, and n denotes an average value of 1–7. A preferable value of n in formula (III), i.e., an average number of moles of ethylene oxide, is in the range of 2–5.

From the aspect of detergency and cost, alkylbenzene sulfonates represented by the following formula (IV) are preferable,

wherein $R_9$ represents an alkyl group having 10 to 16 carbon atoms and M has the same meaning as defined above. A more preferable carbon number of $R_9$ in formula (IV) is in the range of 11–13.

For sulfobetaine, those represented by the following formula (V) are preferable, $$\begin{matrix} R_{11} & X \\ | & | \\ R_{10}-N^+CH_2CHCH_2SO_3^- \\ | \\ R_{12} \end{matrix} \qquad (V)$$

wherein $R_{10}$ represents an alkyl or alkenyl group having 10 to 18 carbon atoms, $R_{11}$ and $R_{12}$ individually represent an alkyl group having 1 to 2 carbon atoms, and X represents a hydroxyl group or a hydrogen atom.

Component (b) is formulated in an amount of 0.1–40% by weight, preferably 0.5–20% by weight. It is preferable that component (b) be formulated in an amount of 10–20% by weight into light-duty detergents for clothing and 0.5–10% by weight, particularly preferably 1–8% by weight, into dishwashing detergents, and shampoos.

Amine oxides, component (c) of the present invention, are compounds represented by formula (III). Among them, alkyldimethylamine oxides having 12–14 carbon atoms are particularly preferable.

Component (c) is formulated in an amount of 0.1-10% by weight, preferably 0.5-7% by weight. A particularly preferable range is 1-4% by weight.

A preferable ratio by weight of components [(b)+(c)/(a)] used in the detergent composition of the present invention is in the range of 1/25-10/1. A preferable range by weight of the ratio (c)/(b) is 1/10-3/1, with the most preferable range being 1/10-1/1.

Given as examples of an ethoxylated nonionic surface active agent, component (d) of the present invention, are polyoxyethylene alkyl ether, polyoxyethylene alkylphenyl ether, polyoxyethylene sorbitan fatty acid ester, polyoxyethylene sorbit fatty acid ester, polyoxyethylene glycol fatty acid ester, polyoxyethylene polyoxypropylene alkyl ether, polyoxyethylene castor oil, polyoxyethylene alkylamine, polyoxyethylene fatty acid amide (moles of ethylene oxide: greater than 10), and the like. Among them, polyoxyethylene alkyl ether having an average 2-30 moles of ethylene oxide and an alkyl group carbon atom number of $C_{8-18}$, and polyoxyethylene alkyl ether having an average 2-20 moles of ethylene oxide and an alkyl group carbon number of $C_{9-12}$ are preferable.

A preferable amount of component (d) to be formulated is in the range of 0.1-10% by weight, with a particularly preferable range being 1-8% by weight. If the amount formulated is less than 0.1% by weight, the detergent composition can only exhibit insufficient performance. While if the amount is greater than 10% by weight, the stability of the detergent composition is reduced.

In addition, a more improved stability in color and odor of the detergent composition can be obtained by incorporating, in addition to the above components (a)-(d), the following components (e) and (f), (e) 0.01-3% by weight of a terpene type hydrocarbon selected from the group consisting of mono-terpene and sesqui-terpene, and (f) 0.0001-0.1% by weight of one or more of 3-isothiazolones represented by the following formulae (VI) and (VII,), or their derivatives,

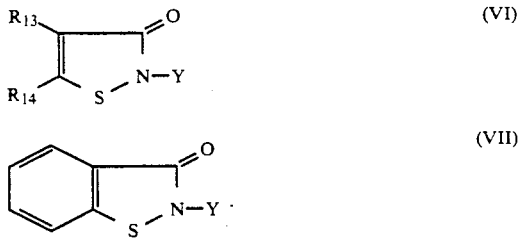

wherein $R_{13}$ and $R_{14}$ respectively represent a hydrogen atom, a halogen atom, or an alkyl group having 1 to 5 carbon atoms, and Y represents a hydrogen atom or an alkyl group having 1 to 18 carbon atoms.

Mono-terpene type or sesqui-terpene type hydrocarbons included in aromatic oils of plant are given as examples of component (e) of the present invention. Given as examples of a mono-terpene type hydrocarbon are D- or L-limonene included in orange oil or lemon oil, α- or β-pinene included in terpene oil, α-terpineol included in pine oil, and the like. Given as examples of a sesqui-terpene type hydrocarbon are caryophyllene and cedrene included in a greater amount in fern oil, clover oil, cananga oil, and the like. Terpene type hydrocarbons can be used for component (e) of the present invention either alone or in the mixture of one or more of them. Furthermore, it is possible to incorporate orange oil, terpene oil, pine oil, or the like as is into the compositions of the present invention. The amount of component (e) to be formulated is in the range of 0.01-3% by weight of the detergent composition, preferably in the range of 0.1-2% by weight, with particularly preferable range being 0.1-1% by weight. If the amount of component (e) to be formulated is less than 0.01% by weight, improvement in solution color- and odor-deterioration due to storage for a prolonged period of time, which is an object of the present invention, is insufficient. While if the amount exceeds 3% by weight, the coloration and the low-temperature stability of the detergent compositions become worse.

3-Isothiazolones represented by formulae (VI) or (VII) or their derivatives, component (f) of the present invention, can give an outstanding effect on preventing color and odor the detergent composition from being deteriorated.

Such an effect is exhibited when the pH of the detergent composition is in the range of 4-10 and little or no effect is exhibited when the pH is outside this range Such a pH dependence is considered to be related to the stability of 3-isothiazolone or its derivative in the detergent composition.

3-Isothiazolone or its derivative is required to be incorporated in an amount of 0.0001-0.1% by weight, particularly 0.005-0.05% by weight, into the detergent composition of the present invention. An amount of less than 0.0001% by weight can only give insufficient effect. While if the amount exceeds 0.1% by weight, irritation to the skin increases.

Beside the above essential components, other optional components can be added to the detergent composition of the present invention to the extent they do not impair the intended effect on the detergent composition. Such optional components include viscosity adjusting agents, e.g. ethyl alcohol, glycerol, propylene glycol, inorganic salts; hydrotropic agents, e.g. lower alkylbenzene sulfonates, urea, lower alkyl sulfates; viscosity controlling agents, e.g. clay minerals, water-soluble polymers; water-insoluble abrasives, e.g. calcite, silica, calcium phosphate, zeolite, polyethylene, nylon, polystyrene; moisturizing agents, e.g. glycerol, sorbitol; feel-improving agents, e.g. cationized cellulose; as well as enzymes, perfumes, coloring agents, preservatives, antifungal agents, and the like.

The pH range of the detergent composition of the present invention is between 4 and 10, with an especially preferable pH range being between 5 and 8.

Other features of the invention will become apparent in the course of the following description of the exemplary embodiments which are given for illustration of the invention and are not intended to be limiting thereof.

EXAMPLES

Test Methods and Standards of Evaluation (1) Foaming ability

Foaming ability was measured using a 0.5% solution of a detergent composition to which 0.1% of commercially available butter was added as a dirt component. 40 ml of this solution was placed in a glass cylinder with a 5 cm diameter and was stirred for 10 minutes. Height of the foam produced was measured immediately after termination of the stirring.

(2) Detergency

Beef tallow to which 0.1% of Sudan III (red color pigment) was added as an indicator was used. 2.5 g of the beef tallow was applied onto each porcelain dishes with a 25 cm diameter. The dishes were then rubbed at a temperature of 20° C with a sponge into which 3 g of a detergent composition and 27 g of water (hardness: 3.5° DH) were absorbed. The number of dishes of which beef tallow dirt could be removed with the sponge was taken as the detergency of the detergent composition.

(3) Rinse-out Performance

Three (3) liters of a 0.25% solution of a sample detergent composition was charged into a vat with a diameter of 30 cm, 12 cm deep, and stirred for 10 minutes to produce foam. The liquid was discharged from a cock at the bottom of the vat. 3 liters of city water were then charged to the vat and stirred for 10 minutes. The liquid was discharged again. This same procedure was repeated until no foam was observed in the vat after the discharge of the liquid. The number of times required to charge 3 liter city water and to discharge the liquid until no residual foam was observed was taken as a standard for the rinse-out performance of a detergent composition.

(4) Hand feel during and after use

Two detergent compositions A and B were provided for the test. Detergent solutions of 10% concentration were prepared from each detergent composition. They were charged into 2 liter beakers at 40° C. and feel of the detergent compositions was evaluated according to the following standard:

(i) Feel during use

The subject immersed right and left hands separately into either the detergent solution A or the detergent solution B, and after 1 minute the feel to the hands of Detergent B in relation to Detergent A was evaluated and rated according to the following criteria:

| | |
|---|---|
| Detergent B is less slippery | +2 |
| Detergent B is slightly less slippery | +1 |
| Cannot tell which is more slippery | ±0 |
| Detergent B is slightly more slippery | −1 |
| Detergent B is more slippery | −2 |

(ii) Feel after use

After the detergent was thoroughly rinsed away, the hands were dried with towel. Then, the feel to the hands of Detergent B in relation to Detergent A were evaluated and rated according to the following criteria:

| | |
|---|---|
| Detergent B is less sticky | +2 |
| Detergent B is slightly less sticky | +1 |
| Cannot tell which is more sticky | ±0 |
| Detergent B is slightly more sticky | −1 |
| Detergent B is more sticky | −2 |

The above tests were performed on ten subjects. The feel imparted by Detergent B was assessed by the sum of the ratings obtained in the above tests (i) and (ii).

(5) Hand skin roughness test

A solution containing 5% by weight of the detergent composition was prepared. The subjects' hands were dipped in the solution for 20 minutes at the solution temperature of 30° C. every day for consecutive 3 days. The conditions of the hands of the 5 subjects were observed with the naked eye on the fourth day and rated according to the following criteria. The results were shown by the mean value of the rating. A mean value 4 or more is desirable in this test.

| | |
|---|---|
| No roughness on the hands was observed | 5 |
| Roughness was very slight | 4 |
| Roughness was observed but not considerable | 3 |
| Considerable roughness was observed | 2 |
| Roughness was remarkable | 1 |

(6) Stability of solution color and odor

The detergent composition was placed in a 50 ml glass bottle. After it was stored in a thermostat at a temperature of 50° C. for one month, the solution color and odor were evaluated.
A: No change was observed
B: Slight change was observed
C: Considerable change was observed
D: Remarkable change was observed

EXAMPLE 1

Compositions shown in Table 1 were prepared, and their foaming capability, detergency, rinse-out performance, hand feel during and after the use, and hand skin roughness were evaluated for each composition. The results are presented in Table 1.

In the evaluation tests, Comparative Product No. 10 was used as Detergent A for comparison of performances of Detergent B (Invention Product Nos. 1-6 and Comparative Product Nos. 7-9).

TABLE 1

| Components | | | Invention Product Nos. | | | | | | % by weight Comparative Product Nos. | | | |
|---|---|---|---|---|---|---|---|---|---|---|---|---|
| | | | 1 | 2 | 3 | 4 | 5 | 6 | 7 | 8 | 9 | 10 |
| Component (a) | $R_1$ | $y$ | | | | | | | | | | |
| Alkyl glycoside: (I) $R_1(OR_2)_xG_y$, $x = 0$, | $C_9$-$C_{11}$ alkyl | 1.1 | 20 | | 15 | | 15 | | | 15 | | |
| G = glucose residue | $C_9$-$C_{11}$ alkyl | 1.4 | | 20 | | 15 | | 15 | | | 15 | |
| | $C_9$-$C_{11}$ alkyl | 2.3 | | | | | | | 20 | | | |
| Component (b) | | | | | | | | | | | | |
| Sodium polyoxyethylene(EO = 3) laurylether sulfate | | | 2 | | 1 | 2 | 2 | | | | | 15 |
| Sodium linear alkyl($C_{12-14}$) benzene sulfonate | | | | 2 | | | | | 2 | | | |
| Sodium α-olefin($C_{12-14}$) sulfonate | | | | | 5 | | 1 | | | 5 | | 5 |

TABLE 1-continued

| Components | Invention Product Nos. 1 | 2 | 3 | 4 | 5 | 6 | Comparative Product Nos. 7 | 8 | 9 | 10 |
|---|---|---|---|---|---|---|---|---|---|---|
| Sodium alkane($C_{12-14}$) sulfonate | | | | 1 | | | | 5 | | |
| Component (c) | | | | | | | | | | |
| $C_{12}H_{25}\overset{O}{\underset{\uparrow}{N}}(CH_3)_2$ | 2 | | | 2 | | | | | | 2 |
| $C_{11}H_{23}CONHCH_2CH_2\overset{O}{\underset{\uparrow}{N}}(CH_3)_2$ | | 2 | | | 2 | | | | 3 | |
| $(C_8H_{17})_2\overset{O}{\underset{\uparrow}{N}}(CH_2CH_2O)_3H$ | | | 3 | | | 1 | 2 | | | |
| Component (d) | | | | | | | | | | |
| $C_{12}H_{25}O(CH_2CH_2O)_{13}H$ | 3 | | | 5 | | | | 5 | | 3 |
| $C_{11}H_{23}CONH(CH_2CH_2O)_{11}H$ | | 3 | | | 3 | 3 | | | | |
| $CH_2-O-COC_{14}H_{29}$ $\|$ $CH-O-(CH_2CH_2O)_{10}H$ $\|$ $CH_2O-(CH_2CH_2O)_{10}H$ | | | 3 | | | | 3 | | | |
| Water | Balance | " | " | " | " | " | " | " | " | " |
| Detergency (number of dishes) | 10 | 10 | 9 | 9 | 9 | 9 | 5 | 4 | 4 | 8 |
| Foaming ability (mm) | 98 | 95 | 95 | 93 | 95 | 92 | 80 | 73 | 68 | 85 |
| Rinsing performance (times) | 5 | 5 | 5 | 5 | 5 | 5 | 8 | 8 | 8 | 10 |
| Hand feel | | | | | | | | | | |
| During use | +12 | +12 | +11 | +11 | +11 | +11 | +3 | +5 | +5 | ±0 |
| After use | +12 | +11 | +11 | +11 | +10 | +11 | +3 | +5 | +5 | ±0 |
| Hand skin roughness | 4.8 | 4.8 | 4.8 | 4.7 | 4.8 | 4.6 | 2.3 | 2.0 | 2.9 | 1.5 |

EXAMPLE 2

| Shampoo (for the hair or the body) | |
|---|---|
| Alkyl glycoside[1] | 15% by weight |
| Polyoxyethylene (EO = 4) laurylether sulfuric acid triethanol amine salt | 3 |
| Monolauric acid monotriethanol amine salt | 3 |
| Myristyldimethyl amine oxide | 2 |
| Softhanol 70[2] | 2 |
| Polymer JR400[3] | 0.2 |
| Ethanol | 3 |
| Perfume, Coloring agent | Appropriate amount |
| Water | Balance |
| | 100 |

[1] Alkyl glycoside: $R_1(OR_2)_xG_y$
 $x = 1$, $y = 1.2$, $R_1 = C_{10}\text{-}C_{13}$, $R_2 = C_2$
 G = Glucose residue
[2] Trademark (ethoxylated nonionic surface active agent manufactured by NIPPON SHOKUBAI KAGAKU KOGYO CO., LTD.)
[3] Trademark (cationized cellulose manufactured by UCC)

EXAMPLE 3

| Light-duty liquid detergent for clothing | |
|---|---|
| Alkyl glycoside[4] | 10% by weight |
| Sodium linear alkyl ($C_{12-14}$) benzene sulfonate | 10 |
| Sodium α-olefin ($C_{12-14}$) sulfonate | 5 |
| Amizet 10C[5] | 2 |
| Lauryldimethyl amine oxide | 2 |
| Latex (Average particle diameter: 0.5μ) | 0.5 |
| Ethanol | 5 |
| Perfume, Coloring agent | Appropriate amount |
| Water | Balance |
| | 100 |

[4] Alkyl glycoside: $R_1(OR_2)_xG_y$
 $x = 1$, $y = 1.1$, $R_1 = C_{10}\text{-}C_{12}$
 G = Glucose residue
[5] Trademark (ethoxylated nonionic surface active agent manufactured by Kawaken Fine Chemical Co., Ltd.)

EXAMPLE 4

| Bathroom detergent | |
|---|---|
| Alkyl glycoside[6] | 4% by weight |
| Hydroxysulfobetaine[7] | 2 |
| Dihexylmethyl amine oxide | 0.5 |
| Emulgen 120[8] | 1 |
| Citric acid | 4 |
| Perfume, Coloring agent | Appropriate amount |
| Water | Balance |
| | 100 | pH = 5.0
[6] Alkyl glycoside: $R_1(OR_2)_xG_y$
 $x = 0$, $y = 1.4$, $R_1 = C_8\text{-}C_{12}$
 G = Glucose residue
[7] $C_{12}H_{25}\overset{-}{N}(CH_3)_2CH_2\underset{\underset{OH}{|}}{CH}CH_2SO_3^-$
[8] Trademark (ethoxylated nonionic surface active agent manufactured by Kao Corporation)

EXAMPLE 5

Compositions into which base components shown below were incorporated together with components (e) and (f) shown in Table 2 were prepared, and solution color and odor were evaluated. The results are presented in Table 2.

| Base composition | |
|---|---|
| Alkyl glycoside[9] | 25% by weight |
| Sodium polyoxyethylene (EO = 4) alkyl($C_{12-13}$) ether sulfate[10] | 5 |
| Lauryldimethyl amine oxide | 3 |
| Polyoxyethylene (EO = 13) lauryl ether | 7 |
| Component (e) | Shown in TABLE 2 |
| Component (f) | Shown in TABLE 2 |
| Ethanol | 5 |
| Water | Balance |
| | 100 |

[9] Alkyl glycoside: $R_1(OR_2)_xG_y$
x = 0, y = 1.3, $R_1$ = $C_9$-$C_{12}$
G = Glucose residue
[10] The ratio of a linear alkyl/branched alkyl: 50/50 by weight

TABLE 2

| | Invention Product Nos. | | | |
|---|---|---|---|---|
| | 11 | 12 | 13 | 14 |
| Component (e) | | | | |
| D-limonene | 0.2 | — | 0.1 | |
| α-pinene | | | | 0.5 |
| Component (f) | | | | |
| 4-benzo-3-isothiazolone | — | 0.01 | 0.01 | |
| Mixture of isothiazoline derivatives[11] | | | | 0.03 |
| Stability | | | | |
| Color | B | C | A | A |
| Odor | C | B | A | A |

[11] A mixture of one part of 5-chloro-2-methyl-4-isothiazoline-3-one and one part of 2-methyl-4-isothiazoline-3-one The detergent composition comprising components (a)-(d) of the present invention exhibits superior detergency and excellent foaming ability. It is mild to the skin causing no or very little roughening of the hands. The detergent composition possesses improved rinse-out performance and imparts better feeling to the hands during washing. It is thus a low irritant detergent composition which is very valuable in practical use. Furthermore, the detergent composition comprising components (a)-(f) of the present invention is more valuable in practical use owing to its added capability of preventing solution color and odor from being deteriorated during storage for a prolonged period of time.

Obviously, numerous modifications and variations of the present invention are possible in light of the above teachings. It is therefore to be understood that within the scope of the appended claims, the invention may be practiced otherwise than as specifically described herein.

What is claimed is:

1. A detergent composition comprising:
    (a) 1-60% by weight of an alkyl glycoside represented by formula (I):

$$R_1(OR_2)_xG_y \quad (I)$$

wherein $R_1$ is a linear or branched alkyl, alkenyl, or alkylphenyl group having 8 to 18 carbon atoms, $R_2$ is an alkylene group having 2 to 4 carbon atoms, G is a moiety derived from a reducing saccharide containing 5 to 6 carbon atoms, x is an average value of 0-5, and y is an average value of 1.0-1.42;
    (b) 0.1-40% by weight of a surface active agent comprising a sulfate group, sulfonate group, or both;
    (c) 0.1-10% by weight of an amine oxide represented by formula (II):

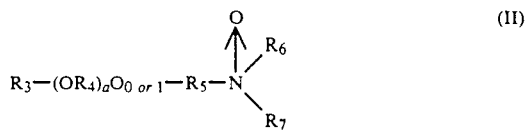

wherein $R_3$ is a linear or branched alkyl or alkylamide group having 8 to 18 carbon atoms, $R_4$ is an alkylene group having 2 to 3 carbon atoms, a is a number from 0-30, $R_5$ is an alkylene group having 0 to 5 carbon atoms, and $R_6$ and $R_7$, which may be the same or different, are each a member selected from the group consisting of alkyl groups having 1 to 12 carbon atoms, alkanol groups having 1 to 3 carbon atoms, $—(C_2H_4O)_{1-6}H$ groups, and mixtures thereof,
    (d) 0.1-10% by weight of an ethoxylated nonionic surface active agent; wherein the ratio by weight of [(b)+(c)]/(a) is in the range of 1/25-10/1 and the ratio by weight of (c)/(b) is 1/10-3/1;
    (e) 0.01-3% by weight of a terpene hydrocarbon selected from the group consisting of monoterpenes and sesquiterpenes, and
    (f) 0.0001-0.1% by weight of one or more 3-isothiazolones represented by formulae (VI) and (VII), or their derivatives,

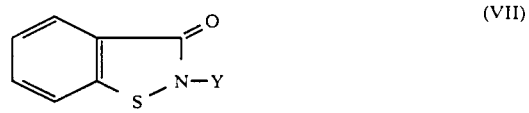

wherein $R_{13}$ and $R_{14}$, individually, are a hydrogen atom, a halogen atom, or an alkyl group having 1 to 5 carbon atoms, and Y is a hydrogen atom or an alkyl group having 1 to 18 carbon atoms.

2. The detergent composition according to claim 1 wherein component (b) is one or more of a compound selected from the group consisting of polyoxyethylene alkylether sulfate, alkylbenzene sulfonate, α-olefin sulfonate, alkane sulfonate, and sulfobetaine.

3. The detergent composition according to claim 1, wherein component (c) is alkyldimethylamine oxide.

4. The detergent composition according to claim 1, wherein component (d) is polyoxyethylene alkylether or polyoxyethylene alkylphenylether.

* * * * *